US012626193B2

(12) United States Patent (10) Patent No.: US 12,626,193 B2
Ghosh et al. (45) Date of Patent: May 12, 2026

(54) ADAPTING A MACHINE LEARNING MODEL BASED ON A SECOND SET OF TRAINING DATA

(71) Applicant: KONINKLIJKE PHILIPS N.V., Eindhoven (NL)

(72) Inventors: Erina Ghosh, Cambridge, MA (US); Larry James Eshelman, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 599 days.

(21) Appl. No.: 16/962,599

(22) PCT Filed: Apr. 16, 2019

(86) PCT No.: PCT/EP2019/059718
§ 371 (c)(1),
(2) Date: Jul. 16, 2020

(87) PCT Pub. No.: WO2019/211089
PCT Pub. Date: Nov. 7, 2019

(65) Prior Publication Data
US 2021/0042667 A1 Feb. 11, 2021

Related U.S. Application Data

(60) Provisional application No. 62/664,365, filed on Apr. 30, 2018.

(51) Int. Cl.
*G16H 10/40* (2018.01)
*G06N 5/02* (2023.01)
*G06N 20/00* (2019.01)
*G06N 20/20* (2019.01)
(Continued)

(52) U.S. Cl.
CPC ............. *G06N 20/20* (2019.01); *G16H 10/60* (2018.01); *G16H 50/70* (2018.01)

(58) Field of Classification Search
CPC ......... G06N 20/20; G16H 10/60; G16H 50/70
See application file for complete search history.

(56) References Cited

U.S. PATENT DOCUMENTS

| | | | | |
|---|---|---|---|---|
| 5,923,004 | A | 7/1999 | Christy et al. | |
| 11,195,616 | B1 * | 12/2021 | Seemakurty | G16H 70/60 |
| 2005/0262031 | A1 | 11/2005 | Saidi et al. | |

(Continued)

FOREIGN PATENT DOCUMENTS

| | | |
|---|---|---|
| AU | 2002233052 B2 | 6/2004 |
| CN | 107256393 A | 10/2017 |

OTHER PUBLICATIONS

International Search Report for PCT/EP2019/059718 dated Apr. 16, 2019.

*Primary Examiner* — Brandon S Cole

(57) ABSTRACT

Systems and methods for adapting a first machine learning model that takes clinical data as input, based on a second set of training data. The first machine learning model having been trained on a first set of training data. The method comprises adding an adaption module to the first machine learning model, the adaption module comprising a second machine learning model, and training the second machine learning model using a second set of training data to take an output of the first machine learning model as input and provide an adjusted output.

15 Claims, 4 Drawing Sheets

(51) Int. Cl.
G16H 10/60 (2018.01)
G16H 50/70 (2018.01)

(56) References Cited

U.S. PATENT DOCUMENTS

| 2008/0059391 | A1* | 3/2008 | Rosales ................. G16H 50/20 |
| | | | 703/2 |
| 2010/0332249 | A1 | 12/2010 | Chbat et al. |
| 2014/0279754 | A1* | 9/2014 | Barsoum ................. G06N 7/01 |
| | | | 706/12 |
| 2015/0006088 | A1 | 1/2015 | Cao et al. |
| 2015/0379430 | A1* | 12/2015 | Dirac .................... G06N 20/00 |
| | | | 706/12 |
| 2017/0140114 | A1 | 5/2017 | Are et al. |
| 2018/0018590 | A1* | 1/2018 | Szeto .................... G06N 20/00 |
| 2018/0046926 | A1* | 2/2018 | Achin .................. G06F 9/5011 |
| 2018/0174043 | A1* | 6/2018 | Po ........................... G06N 3/08 |
| 2018/0366211 | A1 | 12/2018 | Calo et al. |
| 2019/0030371 | A1* | 1/2019 | Han .................... A61N 5/1039 |
| 2019/0251034 | A1* | 8/2019 | Guim Bernat ...... G06F 12/0888 |
| 2020/0387810 | A1* | 12/2020 | Hodgson ............... G16Y 40/20 |

* cited by examiner

ADAPTING A MACHINE LEARNING MODEL BASED ON A SECOND SET OF TRAINING DATA

CROSS-REFERENCE TO PRIOR APPLICATIONS

This application is the U.S. National Phase application under 35 U.S.C. § 371 of International Application No. PCT/EP2019/059718, filed on Apr. 16, 2019, which claims the benefit of U.S. Patent Application No. 62/664,365, filed on Apr. 30, 2018. These applications are hereby incorporated by reference herein.

TECHNICAL FIELD

The disclosure herein relates to a system and method for adapting a machine learning model based on a second set of training data.

BACKGROUND

The general background is in machine learning models used in a clinical setting, e.g. used in clinical decision support systems to make clinical predictions, analyses or diagnoses. Machine learning models (such as empirical-based predictive models) may be trained on specific training data sets, using the characteristic features of the dataset. If, in use, a trained model is used to classify or process data that is not represented in the training data set used to train the model (e.g. new data from a different population compared to the population(s) used to train the model), then it may not perform as well. As such, machine learning models can generally only be used on similar populations to the training data set used to train the model. Since it is very difficult to create a training dataset which encompasses examples of all possible populations (e.g. all different disease types, types of hospitals, geographical and economical settings), such machine learning models may therefore not be appropriate for use with different patient populations e.g. for patients with different chronic conditions, being treated at different hospitals or regions with different care practices.

SUMMARY

As noted above, a machine learning model trained on training data related to a particular patient population may not produce accurate outputs for other patient populations.

One standard approach to address this problem is to train a new model (or re-train an old one using new training data) for each population, e.g. using training data specific to that population. This essentially creates a new model for every dataset on which the model is trained. However, this approach may be resource intensive. It can also result in very different models which may cause problems, for example, if a model needs regulatory approval before it can be deployed. Different models can also make the integration of a model's interface with a workflow more difficult. Furthermore, different versions of a clinical decision support tool will ideally have similar looking outputs for similar patients. These issues may be more problematic if a model is already being used, and one wants to deploy it for patients with different conditions or features.

An alternative approach to re-training a model each time is to train a new model that uses the new conditions/features, and then integrates (e.g. averaging or otherwise combining) the outputs of the two trained models. The state of the art solution for combining the outputs of two or more models is known as "stacking". Although this approach uses the output of the original model, when combined with the output of a second, completely separate model, the combined output may bear little resemblance to that of the original model. This may erode trust in the output and the final outputs may lack transparency e.g. it may not be easy to tell how an output is changed by the stacking process.

There is therefore a need for systems and methods that improve on the solutions described above to enable a machine learning model to be updated based on additional training data, in a transparent and robust way.

According to a first aspect there is provided a method of adapting, based on a second set of training data, a first machine learning model that takes clinical data as input, the first machine learning model having been trained on a first set of training data. The method comprises adding an adaption module to the first machine learning model, the adaption module comprising a second machine learning model, and training the second machine learning model using the second set of training data, to take an output of the first machine learning model as input and provide an adjusted output.

According to a second aspect there is provided a system for adapting, based on a second set of training data, a first machine learning model that takes clinical data as input, the first machine learning model having been trained on a first set of training data. The system comprises a memory comprising instruction data representing a set of instructions and a processor configured to communicate with the memory and to execute the set of instructions. The set of instructions, when executed by the processor, cause the processor to add an adaption module to the first machine learning model, the adaption module comprising a second machine learning model, and train the second machine learning model using the second set of training data, to take an output of the first machine learning model as input and provide an adjusted output.

According to a third aspect there is provided a computer program product comprising a non-transitory computer readable medium, the computer readable medium having computer readable code embodied therein, the computer readable code being configured such that, on execution by a suitable computer or processor, the computer or processor is caused to perform the method of the first aspect.

Adding an adaption module comprising a second machine learning model according to the embodiments herein enables the output of the first machine learning model to be adjusted, based on the second set of training data, rather than re-calculated entirely. Thus the output topology (e.g. the form of the output) of the first machine learning model may broadly be retained, whilst performing an adjustment to take the second set of training data into account. This is helpful, for example, where a model is subject to regulatory approval because the original (regulatory approved) output is broadly retained, and thus just the additional adjustments may require further approval, rather than approval needing to be acquired for an entirely new model each time new training data becomes available.

It will be appreciated that the teachings herein are not merely limited to the clinical domain but may be applied more generally to adjust any pre-trained machine learning model in view of new training data. For example, generally, the teachings herein may be applied to other fields whereby scores (such as risk scores) are calculated using a machine learning model. Thus the teachings herein may be applied, for example, in fields such as finance, accountancy or insurance whereby a credit score or other score describing a risk are calculated. Other possible fields may include meteorology whereby weather reporting is described according to a score or risk.

According to a fourth aspect there is provided a method of adapting, based on a second set of training data, a first machine learning model that takes data as input, the first machine learning model having been trained on a first set of training data. The method comprises adding an adaption module to the first machine learning model, the adaption module comprising a second machine learning model, and training the second machine learning model using the second set of training data, to take an output of the first machine learning model as input and provide an adjusted output.

According to a fifth aspect there is provided a system for adapting, based on a second set of training data, a first machine learning model that takes data as input, the first machine learning model having been trained on a first set of training data. The system comprises a memory comprising instruction data representing a set of instructions and a processor configured to communicate with the memory and to execute the set of instructions. The set of instructions, when executed by the processor, cause the processor to add an adaption module to the first machine learning model, the adaption module comprising a second machine learning model, and train the second machine learning model using the second set of training data, to take an output of the first machine learning model as input and provide an adjusted output.

According to a sixth aspect there is provided a computer program product comprising a non-transitory computer readable medium, the computer readable medium having computer readable code embodied therein, the computer readable code being configured such that, on execution by a suitable computer or processor, the computer or processor is caused to perform the method of the fourth aspect.

These and other aspects of the invention will be apparent from and elucidated with reference to the embodiments described hereinafter.

BRIEF DESCRIPTION OF THE DRAWINGS

For a better understanding and to show more clearly how it may be carried into effect, reference will now be made, by way of example only, to the accompanying drawings, in which.

DETAILED DESCRIPTION OF EMBODIMENTS

Figure 1:
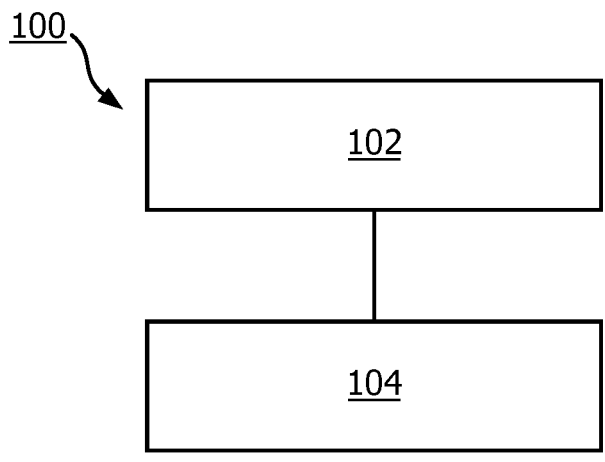
FIG. 1 is a flowchart of an example of a method of adapting, based on a second set of training data, a first machine learning model according to some embodiments herein.

FIG. 1 shows a computer implemented method 100 of adapting, based on a second set of training data, a first machine learning model that takes clinical data as input, according to some embodiments herein. The method 100 is for use on pre-trained models, e.g for use where the first machine learning model has been trained on a first set of training data. The method 100 comprises in a block 102 adding an adaption module to the first machine learning model, the adaption module comprising a second machine learning model. In a second block 104, the method comprises training the second machine learning model using the second set of training data to take an output of the first machine learning model as input and provide an adjusted output.

The first machine learning model may comprise any type of machine learning model such as a logistic regression model, a boosting model (such as Adaboost), a neural network model, or any other machine learning model. The skilled person will generally be familiar with machine learning models. In brief, logistic regression is similar to linear regression except that it may be used to determine a probability, e.g. a normalized score between 0 and 1. A logistic regression model may be used, for example, in embodiments where the first machine learning model is used to output a score such as a risk score (as will be described in more detail below).

With respect to boosting models, a boosting model (or process) works on the premise that it is far easier to create a set of weak classifiers (e.g. weak rules or weak learners) for a classification or regression problem, than a single strong (e.g. more accurate) classifier. However, when combined, a single strong classifier may be determined from such a set of weak classifiers.

Adaboost is a type of boosting process that will also be familiar to the skilled person. An Adaboost model is trained using a set of training data. The training is performed in different rounds, whereby in each round, a different weighting of the training data is used to determine a weak classifier (e.g. a weak rule or weak "learner"). Each piece of training data is initially weighted equally, with the weights of pieces of training data increasing between rounds for pieces whereby the weak classifier fails to make an accurate prediction, in this way, the boosting process pays more attention to training data for which a poor output or prediction is made in each round. The weak classifiers from each round are finally combined into a final strong classifier.

In a (simple) example, each weak classifier may comprise a threshold function that specifies, for different ranges of values of an input parameter, an increment that should be added or subtracted from the final output of the Adaboost model. For example, if the model takes as input a parameter "diabetes status", a weak classifier for this parameter may comprise a threshold function specifying, for example, that if the "diabetes status" is "positive", the Aadaboost model should add 0.2 to the final output and if the "diabetes status" is negative that the Adaboost model should subtract 0.2 from the final output. For a numerical input such as heart rate, a threshold function may specify the Adaboost model to add or subtract an increment from the output depending on where the value of the heart rate falls compared to one or more thresholds (e.g. a weak classifier for heart rate may comprise a threshold function specifying the Adaboost model to increase the output by 0.1 if the heart rate is less than 60 beats per minute, decrease the output by 0.1 if the heart rate is between 60 and 80 beats per minute and decrease the output by 0.2 if the heart rate is higher than 80 beats per minute).

Put formally, the output of the Adaboost model is calculated as follows (e.g. the final "strong classifier" takes the following form):

$$F_T(x) = \Sigma_{t=1}^{T} f_t(x)$$

where each $f_t(x)$ comprises a weak classifier. In other words, the output of an Adaboost model may comprise a summation of a plurality of classifiers, each classifier corresponding to (e.g. comprising a threshold function of) an input parameter.

As noted above, the first machine learning model has been previously trained on a first set of training data. In this sense, the first machine learning model comprises a pre-trained model. The first set of training data used to train the first machine learning model may comprise example clinical data (e.g. example patient data) acquired from a particular group or population of patients, such as patients associated with a particular hospital, hospital system, group of hospitals, geographic location or clinical condition.

The first set of training data may comprise (e.g. be split into) a first set of input parameters (or features). The first set of input parameters may comprise parameters that may be acquired or updated in real-time (for example, readings or measurements from clinical machines or laboratory results). Alternatively or additionally, the first set of input parameters may comprise parameters that may be static, e.g. unchanging with time (e.g. parameters relating to chronic conditions, smoking status, geographic location). More generally, examples of parameters that may be included in the first set of input parameters include readings or measurements from clinical machines (for example, such as readings from heart rate monitors, $SpO_2$ monitors, or any other clinical monitor), clinical images, medical records, or other medical parameters, such as for example, parameters relating to chronic conditions such as the diabetes status of a patient. For each piece of training data (e.g. each set of example values for the first set of input parameters), the first set of training data may further comprise an (example) classification. The classification may have been annotated, pre-calculated or checked by a human. The classification may be thought to represent "ground truth", e.g. an example of the output that the first machine learning model should produce for that piece of training data.

The first machine learning model has been previously trained to produce an output, e.g. the first machine learning model has been previously trained on the first set of training data to determine, for each piece of training data (e,g, each set of values for the first set of input parameters) the respective (example) classification. In some embodiments, the output (e.g. the classification) may be in the form of a score or likelihood (e.g. a percentage likelihood). For example, the output may comprise a risk score describing the likelihood that a patient has, or will develop, a particular condition. For example, the output may describe the risk that a patient will deteriorate (e.g. go into cardiac arrest). The output may comprise a clinical decision support (CDS) score. In other embodiments, the output may comprise any other type of output that may be produced by a machine learning model. For example, the output may relate to a clinical diagnosis, clinical prediction, the location or classification of clinical information.

As noted generally above, the first machine learning model (e.g. the output of the first machine learning model) may have been approved by a regulatory body.

Turning back to FIG. 1, the method 100 may be used to adapt the first machine learning model, based on (e.g. to take account of) a second set of training data. As noted above, block 102 of method 100 comprises adding an adaption module to the first machine learning model, the adaption module comprising a second machine learning model.

In more detail, the second machine learning model may generally comprise any type of machine learning model, such as, for example, a logistic regression model, a boosting model or a neural network as was described above with respect to the first machine learning model. In some embodiments, the second machine learning model may comprise a boosting model (such as an Adaboost model).

In some embodiments the second machine learning model comprises a different type of machine learning model to the first machine learning model. For example, in some embodiments, the first machine learning model may comprise a logistic regression machine learning model and the second machine learning model may comprise a boosting model, such as an Adaboost model.

In block 104 the method comprises training the second machine learning model to take an output of the first machine learning model as input and provide an adjusted output (e.g. such as an adjusted CDS score), based on the second set of training data.

In some embodiments, the second set of training data may comprise additional training data (e.g. additional training examples) that did not form part of the first set of training data. For example, in some embodiments, the second set of training data relates to a patient population. For example, a patient population that is different to the patient population of the first set of training data. In block 104, the method 100 may then comprise training the second machine learning model using (e.g. training the second machine learning model on) the second set of training data to produce the adjusted output.

For example, in some embodiments, the patient population associated with the second set of data may comprise patients associated with one or more of: a hospital, a hospital system, a geographic region, and/or a clinical condition. In this way, the method 100 may be used to adapt a machine learning model (e.g. a model trained on training data taken from an initial population of patients) so as to make the machine learning model suitable for a population of patients (e.g. another population of patients), without the need to retrain an entirely new machine learning model. In this way, the outputs of the adapted first machine learning model are adjusted outputs, rather than entirely new outputs and thus the adjusted output may resemble the output of the first machine learning model which may help with data assurance (particularly if the first machine learning model is subject to regulatory approval).

In some embodiments, the method 100 may further comprise deploying the first machine learning model and the adaption module together for use in producing an adjusted output for the patient population. For example, the trained first machine learning model and the adaption module comprising the trained second machine learning model may be installed on a clinical site or server accessible by a clinician so that they may be used to produce adjusted outputs for new data acquired from patients at that site. A model may thus be produced that is suitable for the population without having to train an entirely new model.

The skilled person will appreciate that this process may be repeated for other patient populations. For example, the method may further comprise repeating the steps of adding and training to produce additional adaption module(s) for other patient population(s).

Additionally or alternatively, the second set of training data may comprise additional input parameters (e.g. additional features) that are different to the first set of input parameters. For example, the first set of training data may comprise a first set of input parameters and the second set of training data may comprise one or more additional input parameters that are different to the parameters of the first set of input parameters. In block 104, the method 100 may comprise training the second machine learning model using the second set of training data to produce an adjusted output, taking the additional input parameters into account.

Generally, the additional input parameters may comprise any type of available data. For example, any of the types of data listed above with respect to the first set of input parameters. For example, the additional input parameters may comprise clinical data (e.g. patient data) such as readings or measurements from clinical machines (for example, such as readings from heart rate monitors, SpO2 monitors, or any other clinical monitor), clinical images, medical records, or other medical parameters, such as for example, parameters relating to chronic conditions such as the diabetes status of a patient. The additional input parameters may comprise parameters that may be acquired or updated in real-time (for example, the aforementioned readings of measurements from clinical machines). Alternatively or additionally, the additional input parameters may comprise parameters that may be static, e.g. generally unchanging on short timescales (e.g. parameters relating to chronic conditions, smoking status, and/or geographic location).

Through the use of additional input parameters in this way, the method 100 may thus be used to adjust the outputs of the first machine learning model when new types of clinical data become available. This might be relevant, for example, where different hospitals or clinical sites have different monitoring equipment or when new or additional medical equipment becomes available that wasn't previously.

Another application of the embodiments herein lies in combining contextual information such as patient history and chronic conditions with patient data from a current hospital stay. Machine learning models may be trained to determine a risk score for the patient, based on features such as vital sign measurements and laboratory results which are measured during a patient's hospital stay. Such parameters are important predictors of future events. However, information on diagnosis, concurrent conditions, chronic history and other such contextual information may modify a patient's risk of deterioration or risk of developing a condition. An adaption module, as described herein, may be used to account for the effect of contextual information in modifying patient's risk factors. Generally therefore, the second machine learning model may be trained to receive "raw" clinical decision support scores and adjust them based on context.

Therefore, in some embodiments, the first set of input parameters may comprise input parameters relating to e.g. real-time clinical measurements (such as heart-rate or SPO2 level) and the additional input parameters may comprise input parameters relating to, for example, a status of a patient, or a static or chronic condition of the patient (e.g. such as diabetes status or weight of the patient). In this way, the method 100 may be used to adapt a machine learning model so as to take account of, or predict the manner in which an output (e.g. determined based on real-time measurements) may require modification in view of a patient's long-term condition or other "static" factor. This may provide insights into the manner in which long-term or static parameters affect an output.

As described above, it is an object of the methods and systems described herein to adjust an output of a trained first machine learning model, whilst preserving as much of the decision process of the first machine learning model as possible. As such, it is desirable for the adjusted output (such as a risk adjusted score) to resemble the output of the first machine learning model (e.g. the "original" output or score), but adjusted in view of the second set of training data (or additional parameters/features of the second set of training data). One goal is for the adjusted output to reflect the output topography (e.g. predictions) of the original model, but somewhat shifted and distorted, reflecting the contributions of the new feature values.

In order to ensure that the output of the second machine learning model preserves the output of the first machine learning model in such circumstances, in some embodiments, the method 100 may further comprise initializing the second machine learning model, using an output of the first machine learning model, such that the second machine learning model produces an equivalent output to the first machine learning model (e.g. for new data) when/if data corresponding to the second set of training data (e.g. data corresponding to the input parameters, or features of the second set of training data) is unavailable. Put another way, the initializing of the second model may ensure the second machine learning model produces the same or equivalent output (e.g. same or equivalent output classification, value or score) when only parameters that were present in the first set of training data are available to make the classification. This means that in the absence of any additional data relating to the parameters comprised in the second set of training data, the second machine learning model will produce equivalent (e.g. the same or similar) outputs as the first machine learning model.

In embodiments where the second machine learning model comprises a boosting model such as an Adaboost model, as described above, the boosting model may be configured to determine the adjusted output based on a summation of a plurality of classifiers. In some embodiments, each classifier may correspond to an input parameter in the second set of training data.

According to some embodiments herein, the boosting model may be configured to apply an initial offset to the summation of the plurality of classifiers, based on the output of the first machine learning model, so as to initialize the boosting model to produce an equivalent output to the first machine learning model if data corresponding to the second set of training data is unavailable. In this way, the initial offset may be used to set an initial state of the boosting model (e.g. such as an Adaboost model).

Put more formally, in some embodiments, the equation for the boosting model, $$F_T(x) = \sum\nolimits_{t=1}^{T} f_t(x)$$

(as described above) may be modified such that the output of the Adaboost model is calculated according to:

$$F_T(x) = m(x) + \sum\nolimits_{t=1}^{T} f_t(x)$$

wherein the term m(x) is an initial offset based on the output of the first machine learning model.

In some embodiments, the method 100 may comprise determining a mapping relationship for converting an output of the first machine learning model into an initial offset (e.g. m(x)).

The mapping relationship may be determined (in a mapping stage) by a mapping model. The mapping model may comprise the same type of machine learning model as the second machine learning model. E,g, if Adaboost is used as the second machine learning model then the mapping model may also comprise an Adaboost model.

The mapping model may be used to determine a mapping from the outputs of the first machine learning model to initial offsets for (the output of) the second machine learning model. For example, if the first machine learning model comprises a logistic regression model and the second machine learning model comprises an Adaboost model, then a mapping model may comprise an Adaboost model that is used to determine a mapping from the logistic regression type scores to initial offsets for Adaboost type scores.

In some embodiments, determining a mapping relationship comprises providing a plurality of outputs of the first machine learning model and a plurality of respective classifications to the mapping model (e.g. by providing mapping training data to the mapping model) and determining a mapping relationship from the output of the mapping model.

For example, the first set of training data may be provided to the mapping model, but instead of inputting the first set of parameters into the mapping model, the outputs of the first model may be input instead, along with the reference (e.g. ground truth) classifications.

In embodiments where the second machine learning model comprises an Adaboost model (and thus the mapping model comprises an Adaboost model), applying the mapping model to such a dataset may produce a threshold function (or step function). In this embodiment, the threshold function may be used to map the output of the first machine learning model to an Adaboost type score that can be used as an initial offset for the second machine learning model.

Turning now to a more detailed example embodiment in which the first machine learning model comprises a logistic regression model and the second model comprises an Adaboost model, the first and second sets of training data may comprise a matrix with a row for each training example (or piece of training data). The first set of columns may comprise the first set of parameters (or features) of the first set of training data used to train the first machine learning model which may be labelled "f1", and the second set of columns may comprise the parameters (or features) of the second set of training data used to train the second machine learning model which may be labelled "f2". (Or alternatively there may be two matrices, an f1 matrix and an f2 matrix, with the same number of rows.) In this example, there may further be a vector of classifications (or class labels) that represent the desired outcome, e.g. the ground truth for each piece of training data. Such a vector may comprise a value for each row in the matrix, e.g. one classification for each piece of training data.

The matrix may be provided to the first machine learning model which produces a vector of outputs, one for each training example, based on the first set of input parameters, f1. The output vector of the first machine learning model may then be provided, along with the vector of classifications to a mapping model (as noted above, the second machine learning model in this embodiment comprises an Adaboost model and therefore the mapping model in this embodiment also comprises an Adaboost model). Applying the mapping model to the output vector of the first machine learning model and the vector of classifications maps the output of the first machine learning model into Adaboost type scores.

The mapping model produces an output vector that is the same length as the input vector and the classification vector (e.g. one mapping value per piece of training data). The values of the output vector of the mapping model are used as initial offset values for the second machine learning model. A mapping lookup table may be generated from the output vector of the first machine learning model and the output vector of the mapping model for determining a mapping relationship.

The matrix (including the output from the module for determining an appropriate mapping) may then be provided to the second machine learning model, which in this example comprises an Adaboost model. The mapped outputs (i.e. the initial offsets) are used to initialize the output vector of the Adaboost model (e.g. before the boosting rounds start) to the scores produced by the weak classifiers from the first machine learning model.

In this way, the output of the first machine learning model is preserved, for example, when there is no f2 parameter data available. Furthermore, the second machine learning model starts from and makes adjustments directly to the output of the first machine learning model. As such, the output topology of the first machine learning model is retained and tweaked or adjusted in view of the second set of training data. This makes the output more transparent and thus helps with data assurance (in the event that the first and or second models require regulatory approval).

Use of mapping in this way initializes the second machine learning model (e.g. the Adaboost model) so that it acts like (e.g. produces the output of) the first machine learning model. The mapping step allows the use of an incremental improvement algorithm for the new algorithm, even though one wasn't used for the original algorithm. In this way, the output of the adapted machine learning algorithm continues to look similar to that of the first machine learning model.

It is noted for completeness that if both the first machine learning model and the second model machine learning model use Adaboost, then no mapping may be necessary since the output from the first machine learning model is in the right form for initializing the second machine learning model. For example, the output of a first Adaboost model may be used directly as an initial offset to initialize a second Adaboost model. If the first machine learning model is trained with Adaboost and the output is used to initialize the second machine learning model (also trained with Adaboost), then this is equivalent to training Adaboost with the first set of features for N1 rounds and the second set of features for the remaining N2 rounds. (And in this case no mapping may be needed.)

Figure 2:
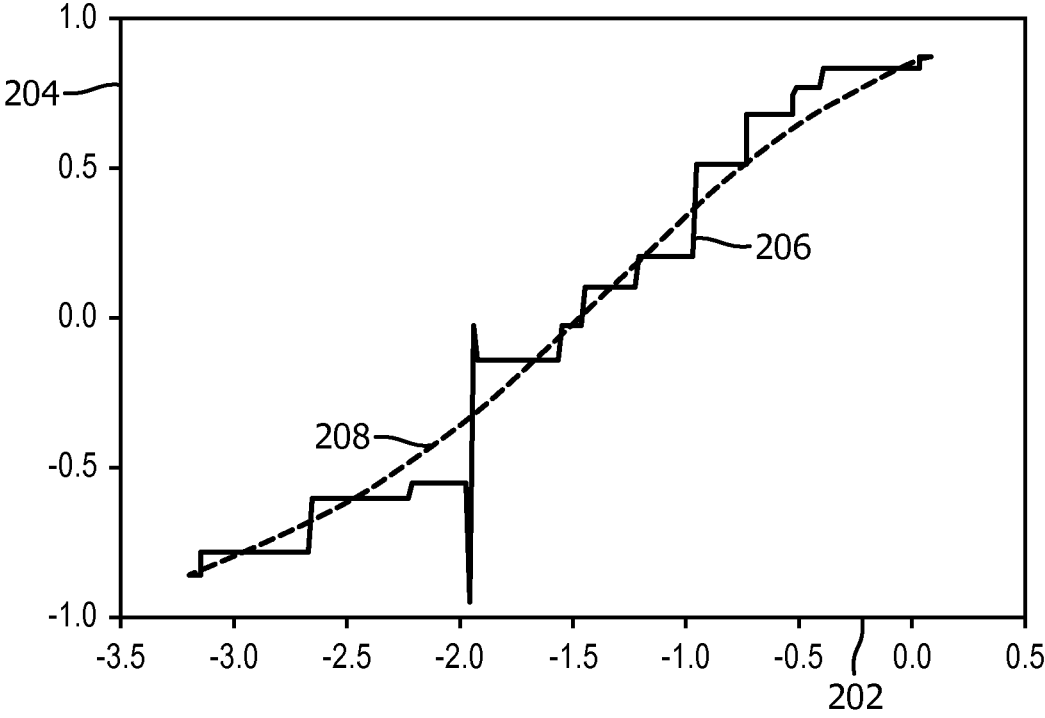
FIG. 2 shows a graph illustrating an example mapping relationship according to some embodiments herein.

An example mapping relationship is shown in FIG. 2 which shows a mapping relationship as illustrated by the line 206 for converting output from a logistic regression output 202 to an Adaboost output 204 according to one example.

In some embodiments, the mapping relationship may be smoothed, as shown by the line 208 in FIG. 2.

Figure 3:
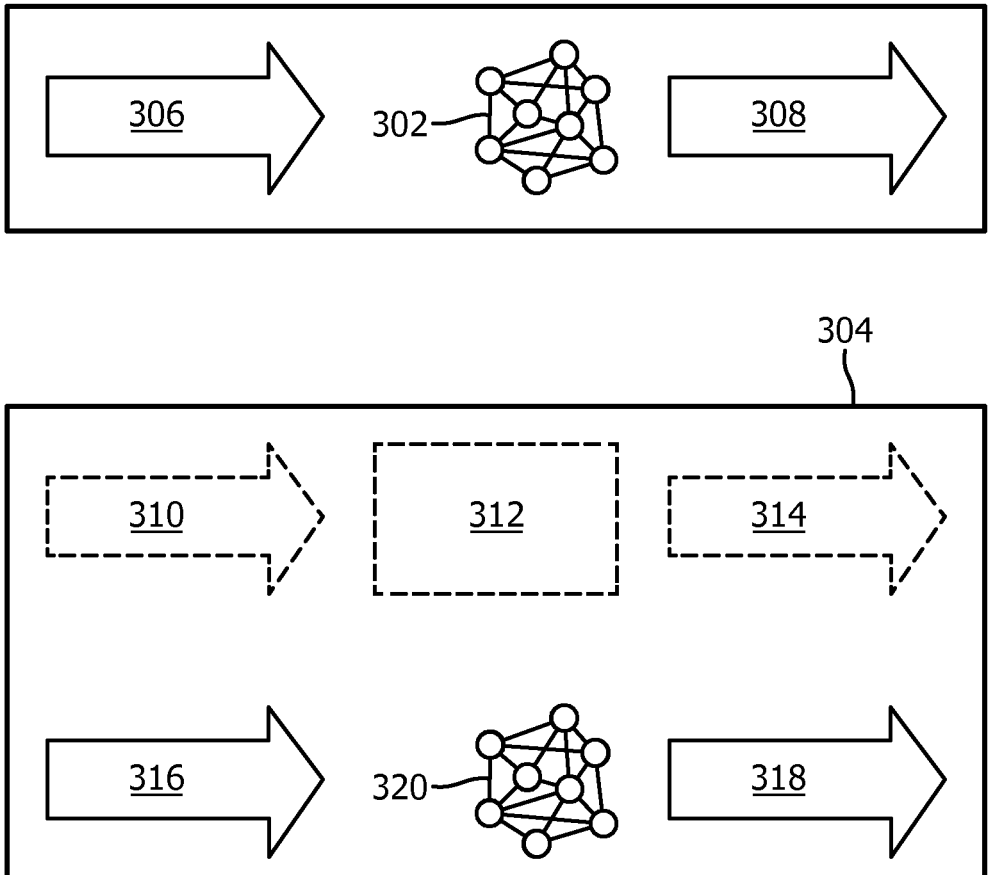
FIG. 3 is a schematic illustration showing the inputs and outputs of a first machine learning model and an adaption module according to example embodiments herein.

Some of the embodiments herein may be summarized in FIG. 3 which shows a first machine learning model 302 according to an embodiment. In this embodiment, the first machine learning model has been trained on a first set of training data. The first machine learning model is trained to take, as input, a first set of input parameters 306 and output one or more outputs 308.

The first machine learning model 302 is adapted, based on a second set of training data, by means of an adaption module 304. The adaption module 304 comprises a second machine learning model 320. In some embodiments, the second machine learning model 320 has been trained, based on the second set of training data, to take an output 308 of the first machine learning model 302 as input 316 (e.g. in some embodiments, the output 308 is the same as the input 316.) In such embodiments, as described above, the output of the first machine learning model is used as an input parameter (e.g. input feature) to the second machine learning model.

In other embodiments, the adaption module 304 further comprises a mapping module 312 comprising a mapping relationship. The mapping module takes as input, the output of the first machine learning model 308 (e.g. in some embodiments, the output 308 is the same as the input 310), maps the output of the first machine learning model to an initial offset 314 and provides the initial offset 314 as an input 316 to the second machine learning model 320 (e.g. in some embodiments, the output 308 of the first machine learning model 302 is mapped before it is input into the second machine learning model 320). In such embodiments, as described above, the initial offset is used by the second machine learning model to initialize the second machine learning model (e.g. instead of being used as an input parameter or feature, the initial offset may be used to set an initial state of the second machine learning model). As described above, the initialization may be performed to ensure that the output of the second machine learning model comprises an adjustment to the output of the first machine learning model (rather than a completely independently derived output).

In this way, according to the embodiments herein, the second machine learning model 320 outputs an adjusted output 318 that may reflect, both the output 308 of the first machine learning model 302 and the second set of training data.

In use, after training 104 the second machine learning model, the first machine learning model and the adaption module (comprising the second machine learning model) may be deployed together for use in determining an adjusted output for new (e.g unseen) clinical data.

In some embodiments, the method 100 therefore further comprises using the adapted machine learning model (e.g. the combination of the first machine learning model and the adaption module comprising the second machine learning model) to produce an adjusted output for new (e.g. previously unseen and not forming part of the first or second training sets) clinical data.

For example, in some embodiments the method may comprise providing new clinical data as input to the first machine learning model, acquiring a new output from the first machine learning model, providing the new output as an input to the adaption module, and receiving a new adjusted output from the adaption module.

In embodiments where, as described above, the second machine learning model comprises a boosting model and the method 100 comprises determining a mapping relationship to convert output values of the first machine learning model into initial offsets, in use, the method may comprise the adaption module mapping the new output to an initial offset, using the determined mapping relationship. The adaption module may then initialize the second machine learning model (e.g. the boosting model), using the initial offset.

Figure 4:
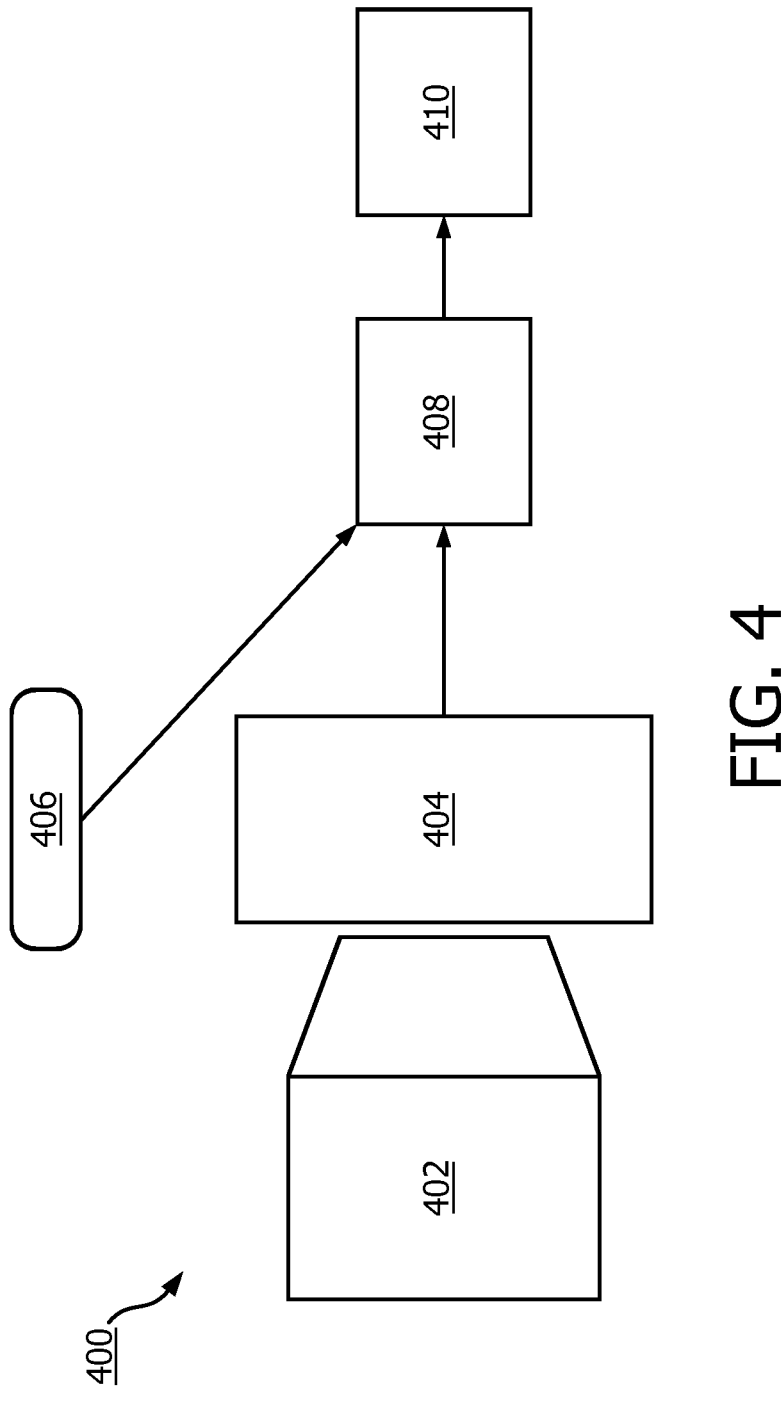
FIG. 4 is a schematic illustration showing the inputs and outputs of a first machine learning model and an adaption module according to example embodiments herein.

This is illustrated in FIG. 4 which shows, in use (e.g. when the first machine learning model is deployed with an adaption module comprising a second machine learning model) the inputs and outputs of a second machine learning model 408 according to an embodiment. In this embodiment, new clinical data 402 is converted into a set of parameters 404 (for example the first set of input parameters and/or the additional input parameters as described above). The parameters may comprise, for example, a diagnosis, aspects of a patient's medical history, an admission type, details of a patient's interventions or procedures and/or details of a patient's medication(s). The parameters 404 are provided as input parameters 404 to the second machine learning model 408. In addition to the N features, a new output 406 of the first machine learning model is also input to the second machine learning model 408. As described above, the new output of the first machine learning model may have been mapped using a mapping relationship as described above to produce an initial offset. Based on these inputs, the second machine learning model 408 determines an adjusted new output 410.

In some embodiments, the method 100 may further comprise outputting the new output 406 and the adjusted new output 410. In this way, the manner in which the output of the first machine learning model was adapted in view of the additional new data may be more easily appreciated. This may help with transparency of the solution and thus user confidence and adoption.

Figure 5:
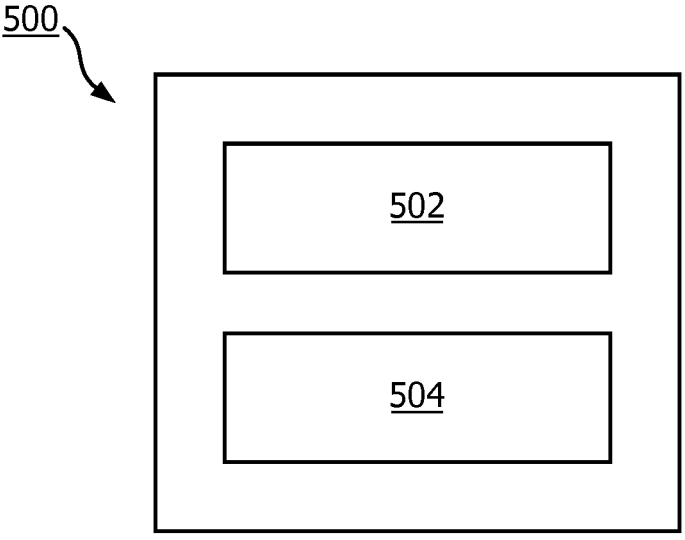
FIG. 5 shows an example system for adapting, based on a second set of training data, a first machine learning model, according to some embodiments herein.

Turning now to FIG. 5, there is a system 500 configured for adapting a first machine learning model based on a second set of training data. The first machine learning model has been trained on a first set of training data and takes clinical data as input. The system 500 comprises a memory 504 comprising instruction data representing a set of instructions. The system 500 further comprises a processor 502 configured to communicate with the memory 504 and to execute the set of instructions. The set of instructions when executed by the processor may cause the processor to perform any of the embodiments of the method 100 as described above.

In some implementations, the instruction data can comprise a plurality of software and/or hardware modules that are each configured to perform, or are for performing, individual or multiple steps of the method described herein. In some embodiments, the memory 504 may be part of a device that also comprises one or more other components of the system 500 (for example, the processor 502 and/or one or more other components of the system 500). In alternative embodiments, the memory 504 may be part of a separate device to the other components of the system 500.

In some embodiments, the memory 504 may comprise a plurality of sub-memories, each sub-memory being capable of storing a piece of instruction data. In some embodiments where the memory 504 comprises a plurality of sub-memories, instruction data representing the set of instructions may be stored at a single sub-memory. In other embodiments where the memory 504 comprises a plurality of sub-memories, instruction data representing the set of instructions may be stored at multiple sub-memories. Thus, according to some embodiments, the instruction data representing different instructions may be stored at one or more different locations in the system 500. In some embodiments, the memory 504 may be used to store information, such as data relevant to calculations or determinations made by the processor 502 of the system 500 or from any other components of the system 500.

The processor 502 can comprise one or more processors, processing units, multi-core processors and/or modules that are configured or programmed to control the system 500 in the manner described herein. In some implementations, for example, the processor 502 may comprise a plurality of (for example, interoperated) processors, processing units, multi-core processors and/or modules configured for distributed processing. It will be appreciated by a person skilled in the art that such processors, processing units, multi-core processors and/or modules may be located in different locations and may perform different steps and/or different parts of a single step of the method described herein.

Briefly, the set of instructions, when executed by the processor 502, cause the processor 502 to add an adaption module to the first machine learning model, the adaption module comprising a second machine learning model. The set of instructions, when executed by the processor 502, further cause the processor 502 to train the second machine learning model using a second set of training data to take an output of the first machine learning model as input and provide an adjusted output. Adding an adaption module to the first machine learning model and training a second machine learning model were described above with respect to the method 100 and the details therein will be understood to apply equally to the operation of the system 500.

According to some embodiments, there is also a computer program product comprising a non-transitory computer readable medium, the computer readable medium having computer readable code embodied therein, the computer readable code being configured such that, on execution by a suitable computer or processor, the computer or processor is caused to perform the method 100.

The term "module", as used herein is intended to include a hardware component, such as a processor or a component of a processor configured to perform a particular function, or a software component, such as a set of instruction data that has a particular function when executed by a processor.

It will be appreciated that the embodiments of the invention also apply to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to embodiments of the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method of adapting outputs of a trained model that preserves the trained model, the method comprising:

identifying a first machine learning model and a second machine learning model, the first machine learning model having been trained on a first set of training data to utilize clinical data as a first phase input and generate, from the first phase input, a first phase output comprising a first vector;

generating, by a mapping module comprising a mapping model of the same type of model as the second machine learning model, an offset vector configured to be included as part of a second phase input to the second machine learning model; and accessing, by an adaption module comprising the second machine learning model the second phase input, the second phase input comprising the offset vector and the first phase output, to generate a second phase output comprising an adjusted classification;

wherein the mapping model is trained using a plurality of first phase outputs and one or more of predetermined offsets or predetermined second phase outputs, and the second machine learning model is trained to generate the adjusted classification using a second set of training data and is configured to accept as input a matrix comprising the offset vector and a vector of the same type as the first phase vector.

2. A method as in claim 1, wherein the second set of training data relates to a patient population.

3. A method as in claim 2, further comprising:

deploying the first machine learning model and the adaption module together for use in producing an adjusted output for the patient population.

4. A method as in claim 1, further comprising:

repeating the adding and training to produce an additional adaption module for another patient population.

5. A method as in claim 1, wherein the first set of training data comprises a first set of input parameters, the second set of training data comprises one or more additional input parameters that are different to the parameters of the first set of input parameters, and wherein the training comprises:

training the second machine learning model using the second set of training data to produce the adjusted output by taking the additional input parameters into account.

6. A method as in claim 1, wherein the second machine learning model comprises a boosting model configured to determine the adjusted output based on a summation of a plurality of classifiers.

7. A method as in claim 6, wherein the boosting model is further configured to:

determine, from the mapping relationship, an initial offset for an unadjusted output from the second machine learning model by converting the output of the first machine learning model into the initial offset for the unadjusted output from the second machine learning model based on the mapping relationship; and apply the initial offset to the summation of the plurality of classifiers, based on the output of the first machine learning model, so as to initialize the boosting model to produce an equivalent output to the first machine learning model if data corresponding to the second set of training data is unavailable.

8. A method as in claim 7, further comprising:

determining a mapping relationship for converting an output of the first machine learning model into an initial offset.

9. A method as in claim 1, wherein determining a mapping relationship comprises:

providing a plurality of outputs of the first machine learning model and a plurality of respective classifications to a mapping model; and determining a mapping relationship from the output of the mapping model.

10. A method as in claim 1, further comprising:

providing new clinical data as input to the first machine learning model;

outputting a new output from the first machine learning model;

providing the new output as an input to the adaption module; and outputting a new adjusted output from the adaption module.

11. A method as in claim 10, further comprising the adaption module:

mapping the new output to an initial offset, using the determined mapping relationship; and initializing the second machine learning model, using the initial offset.

12. A method as in claim 10, further comprising:

outputting the new output and the adjusted new output.

13. A system for adapting outputs of a trained model that preserves the trained model, the system comprising:

a memory comprising instruction data representing a set of instructions;

a processor configured to communicate with the memory and to execute the set of instructions, wherein the set of instructions, when executed by the processor, cause the system to:

identify a first machine learning model and a second machine learning model, the first machine learning model having been trained on a first set of training data to utilize clinical data as a first phase input and generate, from the first phase input, a first phase output comprising a first vector;

generate an offset vector configured to be included as part of a second phase input to the second machine learning model; and access, with an adaption module comprising the second machine learning model, the second phase input, the second phase input comprising the offset vector and the first phase output, to generate a second phase output comprising an adjusted classification;

wherein the mapping model is trained using a plurality of first phase outputs and one or more of predetermined offsets or predetermined second phase outputs, and the second machine learning model is trained to generate the adjusted classification using a second set of training data and is configured to accept as input a matrix comprising the offset vector and a vector of the same type as the first phase vector.

14. A non-transitory computer readable medium that stores instructions, which when executed by one or more processors, cause the one or more processors to:

identify a first machine learning model and a second machine learning model, the first machine learning model having been trained on a first set of training data to utilize clinical data as a first phase input and generate, from the first phase input a first phase output comprising a first vector;

generate an offset vector configured to be included as part of a second phase input to the second machine learning model; and access, with an adaption module comprising the second machine learning model, the second phase input, the second phase input comprising the offset vector and the first phase output, to generate a second phase output comprising an adjusted classification;

wherein the mapping model is trained using a plurality of first phase outputs and one or more of predetermined offsets or predetermined second phase outputs, and the second machine learning model is trained to generate the adjusted classification using a second set of training data and is configured to accept as input a matrix comprising the offset vector and a vector of the same type as the first phase vector.

15. The method as in claim 2, wherein the patient population comprises patients associated with one or more of:

a hospital;

a hospital system;

a geographic region; and a clinical condition.

\* \* \* \* \*